United States Patent [19]
Folkman et al.

[11] Patent Number: 5,019,372
[45] Date of Patent: May 28, 1991

[54] MAGNETICALLY MODULATED POLYMERIC DRUG RELEASE SYSTEM

[75] Inventors: Judah Folkman, Brookline; Robert S. Langer, Jr., Somerville; Dean S. T. Hsieh, Cambridge, all of Mass.

[73] Assignee: The Children's Medical Center Corporation, Boston, Mass.

[21] Appl. No.: 579,050

[22] Filed: Sep. 7, 1990

Related U.S. Application Data

[63] Continuation of Ser. No. 879,914, Jun. 27, 1986, abandoned.

[51] Int. Cl.$^5$ .......................... A61K 9/00; A61K 9/16; A61L 15/03
[52] U.S. Cl. .......................................... 424/9; 128/804; 424/423; 424/424; 424/426; 424/462; 424/450; 424/451; 424/453; 424/470; 424/496; 424/499; 604/890.1; 604/891.1
[58] Field of Search ...................... 128/1.3, 804; 424/9, 424/78, , 426, 450, 490, 496, 497, 422, 423, 424, 451, 453

[56] References Cited

U.S. PATENT DOCUMENTS

| | | | |
|---|---|---|---|
| 3,608,549 | 9/1971 | Merrill | 604/114 |
| 3,659,600 | 5/1972 | Merrill | 604/131 |
| 4,247,406 | 1/1981 | Widder et al. | 424/486 |
| 4,267,234 | 5/1981 | Rembaum | 424/497 |
| 4,269,826 | 5/1981 | Zimmermann et al. | 128/1.3 |
| 4,335,094 | 6/1982 | Mosbach | 424/9 |
| 4,357,259 | 11/1982 | Senyei et al. | 424/450 |
| 4,369,226 | 1/1983 | Rembaum | 424/497 |
| 4,452,773 | 6/1984 | Molday | 424/9 |
| 4,652,257 | 3/1987 | Chang | 128/1.3 |
| 4,674,680 | 6/1987 | Lemelson | 424/490 |
| 4,690,130 | 9/1987 | Mirell | 128/1.3 |

OTHER PUBLICATIONS

Langer et al. J. Membrane Sci. 7: 333–350 (1980) Control of Release Kinetics of Macromolecules from Polymers.
Hsieh et al. Proc. Natl. Acad. Sci. U.S.A. 78(3): 1863–1867, Mar. 1981, Magnetic Modulation of Release of Macromolecules from Polymers.
Langer, Chemtech Feb. 1982, pp. 98–105 Controlled Release of Macromolecules.

Primary Examiner—Shep K. Rose
Attorney, Agent, or Firm—Fish & Richardson

[57] ABSTRACT

A magnetically responsive composition for the modulated, sustained administration of a biologically active substance, the composition being in the form of a body sized and shaped for placement in the environment of use, the environment including an aqueous fluid, the body comprising, in admixture, a first phase comprising a biocompatible, plastically deformable, polymeric matrix, the polymeric matrix being insoluble in the environment of use, a second phase having a biologically active substance distributed throughout the matrix to be released to the aqueous fluid outside the matrix, and a third phase comprising a magnetically responsive substance encapsulated within the matrix so that, upon exposure of the body to an oscillating magnetic field, the rate of release of the biologically active substance to the aqueous fluid is increased.

15 Claims, 3 Drawing Sheets

PREPERATION OF MAGNETIC SUSTAINED RELEASE POLYMER

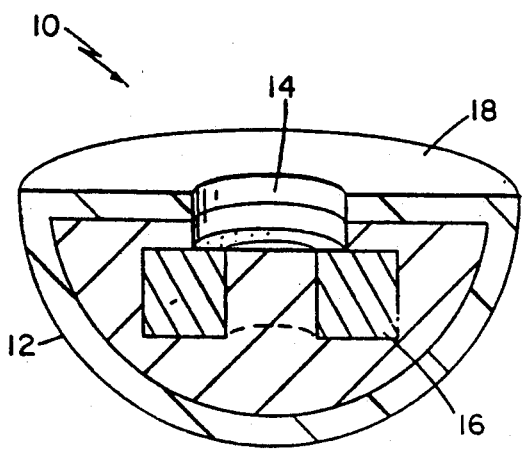
FIG. 4
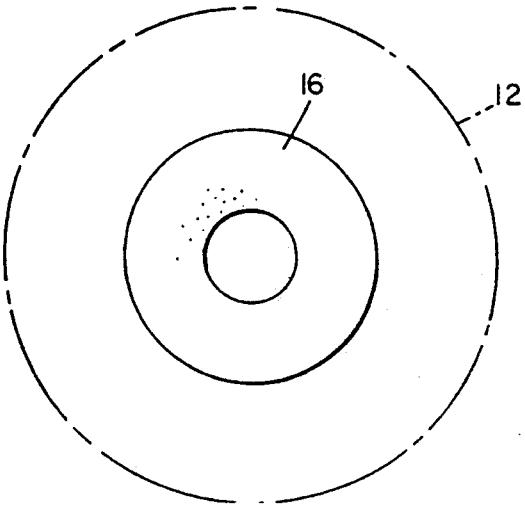
FIG. 5
FIG. 7
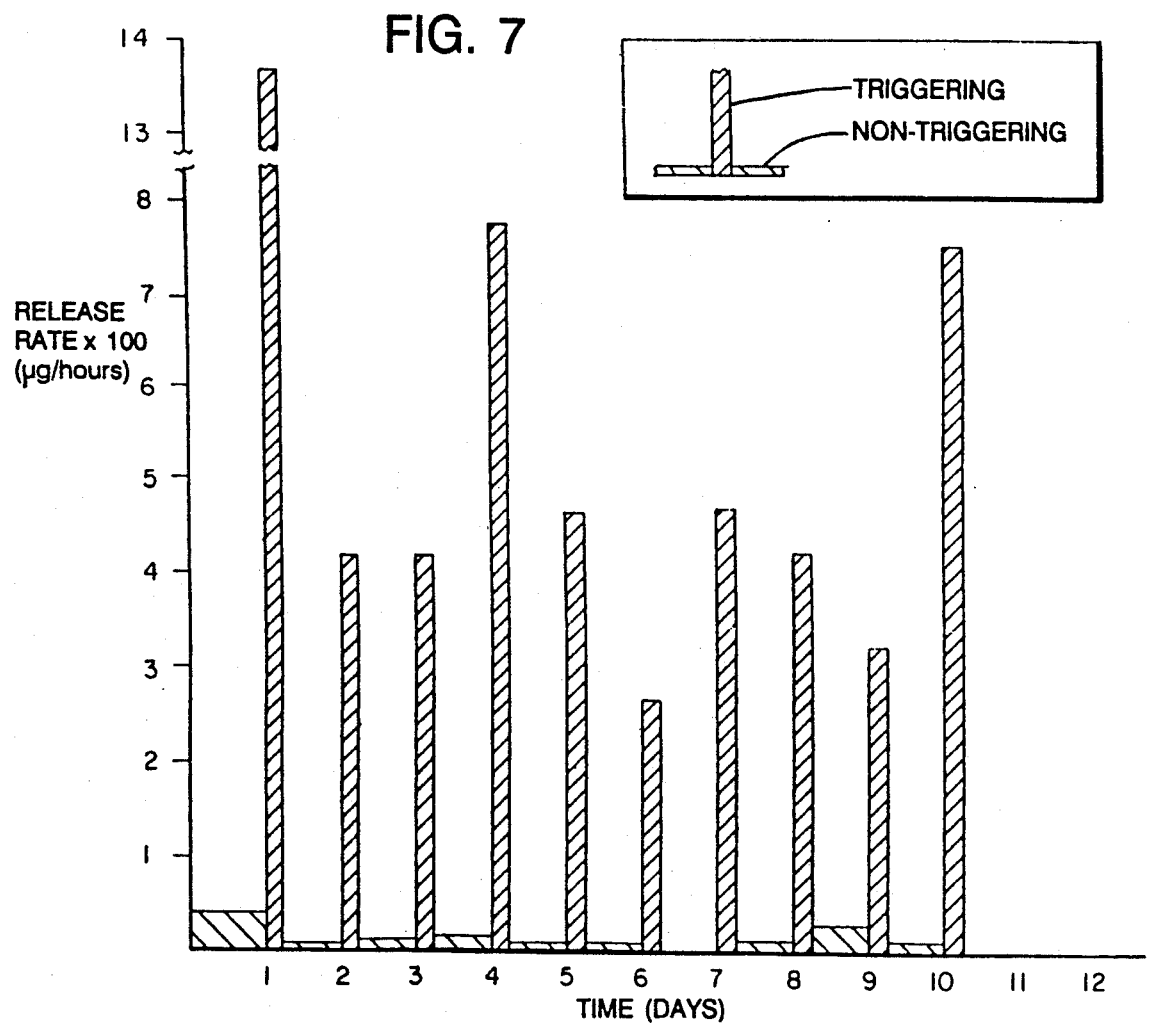

MAGNETICALLY MODULATED POLYMERIC DRUG RELEASE SYSTEM

This is a continuation application under 37 CFR 1.60, of pending application Ser. No. 06/879,914, filed on June 27, 1986, now abandoned.

BACKGROUND OF THE INVENTION

This application is a continuation-in-part of Folkman et al. Ser. No. 113,244, filed Jan. 18, 1980.

This invention relates to systems for sustained delivery of biologically active substances from a polymeric matrix.

Various such systems are described in U.S. Pat. No. 4,164,560 and U.S. patent application Ser. No. 042,788, filed May 29, 1979, which are hereby incorporated by reference.

U.S. patent application Ser. No. 042,788 describes a continuous macromolecule delivery system including a polymer matrix in which there is incorporated an agglomerated, biologically active macromolecular agent. The polymer forming the matrix is biocompatible, plastically deformable, is insoluble in aqueous fluid, is substantially impermeable to the macromolecular agent, and has an aqueous fluid sorptivity not greater than 50% of its weight. The macromolecular agent is hydrophilic and aqueous fluid swellable. When the polymeric body containing the agglomerated macromolecular agent is placed in an aqueous environment, aqueous fluid permeates by diffusion into the polymer matrix and is absorbed by the macromolecules, which swell and exert pressure on the matrix. The matrix has channels communicating between the macromolecular particles and the surface of the polymer body, so that the biologically active macromolecules are continuously released from the matrix over a prolonged period of time.

SUMMARY OF THE INVENTION

In general, the invention features a magnetically responsive composition for the modulated, sustained administration of a biologically active substance, the composition being in the form of a body sized and shaped for placement in the environment of use, the environment including an aqueous fluid, the body comprising, in admixture, a first phase comprising a biocompatible, plastically deformable, polymeric matrix, the polymeric matrix being insoluble in the environment of use, a second phase having a biologically active substance distributed throughout the matrix to be released to the aqueous fluid outside the matrix, and a third phase comprising a magnetically responsive substance encapsulated within the matrix so that, upon exposure of the body to an oscillating magnetic field, the rate of release of the biologically active substance to the aqueous fluid is increased.

In preferred embodiments, the magnetically responsive substance is in the form of discrete particles dispersed throughout the matrix or in the form of a single piece; the ratio, by weight, of the biologically active substance to the polymer is between 1:99 and 90:10; the active substance has a molecular weight of at least 150 daltons; the active substance is a protein; the polymeric matrix is an ethylene-vinyl ester copolymer of the general formula:

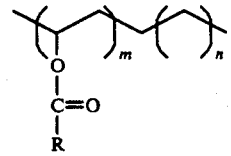

wherein R is a member selected from the group consisting of hydrogen, lower alkyl of 1 to 7 carbons, and aryl, m is (10–40) % by weight, and n is (100-m) % by weight; and the body is in the shape of a hemisphere having a concavity on its flat face, the surface of the concavity being substantially the only surface of the body which permits the release of the biologically active substance to the aqueous fluid, the remaining surface of the body being sealed with a water-impermeable polymeric film.

The invention provides controlled release of any desired active substance to an aqueous environment, e.g., an animal or human patient. The rate of release can be increased at any desired time by simply exposing the polymeric body to an oscillating magnetic field thereby creating sufficient disturbance to increase the release rate of the substance.

Other advantages and features of the invention will be apparent from the following description of the preferred embodiments thereof, and from the claims.

DESCRIPTION OF THE PREFERRED EMBODIMENTS

We turn now to a description of the preferred embodiments of the invention, first briefly describing the drawings.

DRAWINGS

FIG. 4 is a cross-sectional view of a second preferred composition.

FIG. 5 is a plan view of the magnet of said second composition.

FIG. 7 is a graph illustrating the effect of exposure to an oscillating magnetic field on the rate of release of a biologically active substance from said second preferred composition.

MANUFACTURE

Figure 1:
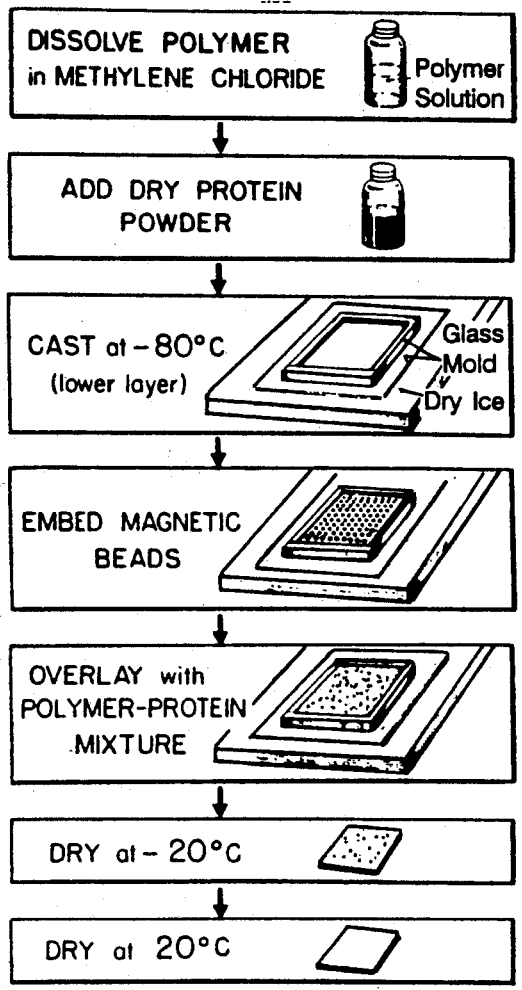
FIG. 1 is a diagrammatic representation of a method of preparing a preferred magnetically responsive composition.

There is shown in FIG. 1 a method of preparing a magnetically responsive composition containing ethylene vinyl acetate copolymer which is 40% vinyl acetate by weight (EVA; available as ELVAX 40 from the DuPont Chemical Company Wilmington, Del.), bovine serum albumin (BSA), and stainless steel beads approximately 1.4 mm in diameter.

A 10 percent (weight/volume) solution of EVA in methylene chloride is prepared for use as the polymer casting solution. One-half gram of powdered BSA, sieved to contain particles between 149 and 210 microns, is suspended in 10 ml of casting solution. The suspension is poured quickly into a leveled glass mold (7×7×0.5 cm) which has been cooled on dry ice for five minutes, so its temperature is about −80° C. The mold remains on the dry ice throughout the procedure.

The stainless steel beads are immediately placed in the polymer mixture using bacterial culture petri dishes (Falcon 1001, Oxnard, Calif.) as follows. Both the lid and the bottom of each dish have an arrangement of 263 holes 1.8 mm in diameter spaced 3 mm apart. The lid of each dish is inverted and placed inside the dish bottom, with the upper and lower holes offset; the dish is then filled with the steel beads. With the dish positioned over the polymer slab in the mold, the lid and bottom are shifted so that the holes align, permitting the beads to drop onto the polymer uniformly.

Two minutes after the magnetic beads are added, a top layer of polymer-BSA mixture is cast over the beads. After the entire mixture has solidified (approximately 10 minutes), the resulting slab is transferred to a −20° C. freezer for 48 hours, and is then dried further at 20° C. under a house-line vacuum (600 millitors) for an additional 24 hours.

The resulting body has a uniform distribution of both the BSA and the steel beads throughout the polymer phase. The slab is 0.8-2.2 mm thick, and has approximately 14 beads in each 1 $cm^2$. Each slab contains approximately (by weight) 1/6 drug, ⅓ polymer and ⅓ magnetic beads.

There is shown in FIG. 4 another preferred embodiment, in which the body 10 is in the shape of a hemisphere having concavity 14 in the center, of its flat face 18. The remaining surface of the body is sealed with EVA coating 12. Hollow cylindrical magnet 16 is encapsulated in EVA/BSA matrix 20.

Figure 6:
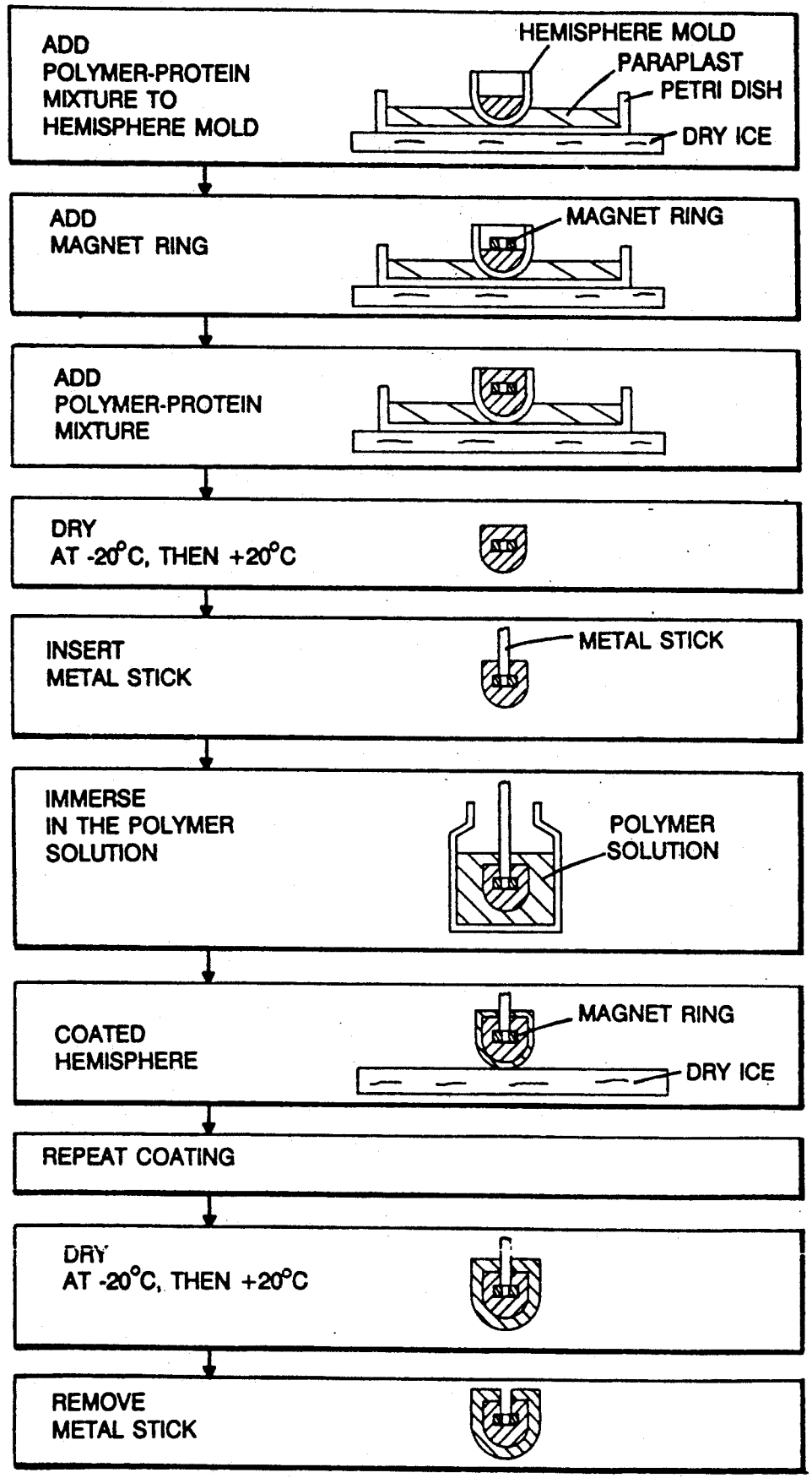
FIG. 6 is a diagrammatic representation of a method of preparing said second composition.

There is illustrated in FIG. 6 a method of making the body of FIG. 4. BSA powder is mixed with 10% EVA to form a mixture which is 33% BSA, w/w; BSA powder and EVA are prepared as described for the previous embodiment.

A first layer of BSA/EVA mixture is cast in a hemispherical mold (13 mm OD×11 mm ID×11 mm high) held in a paraplast supported on a petri dish which has beer cooled for five minutes on dry ice. A single hollow cylinder magnet (3 mm OD×1.5 mm ID×1.5 mm high) is then placed in the center, and a second layer of BSA/EVA mixture is cast onto the magnet. This procedure controls casting so that the magnet does not settle to the bottom, and the two protein-polymer layers adhere tightly.

The hemispheric body is dried in a freezer (−20° C.) for two days and is then dried in a dessicator (20° C.) under a houseline vacuum (600 millitors) for two days. The finished approximately 6 mm in height and 8 mm in diameter. Its composition is approximately 51.5 mg protein, 103. mg polymer and 71.6 mg magnet.

The hemisphere is then twice coated with 20% EVA solution and given its concavity, as follows: (i) a metal stick (1.8 mm diameter×30 mm in length) is inserted at the center of the flat face of the hemisphere to a depth of about 3 mm. (ii) The hemisphere is placed directly on the surface of a block of dry ice for 10 minutes. (iii) Using the metal stick as a handle, the cooled hemisphere is then immersed into 20% EVA solution at 25° C. for 10 seconds, removed, and then placed immediately on the same dry ice for 10 minutes. A second layer of coating is done in the same manner as the first layer of coating. (v) The hemisphere is put in a freezer (−20° C.) for 2 and then dried further for 2 days in a dessicator under a houseline vacuum to remove residual solvent. (vi) The metal stick is then removed by encircling the area around it with a scalpel blade.

OPERATION

Figure 2:
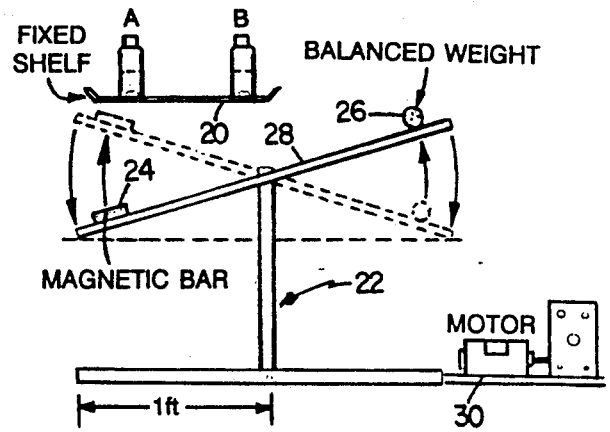
FIG. 2 is a diagrammatic representation of apparatus for measuring rate of release.

There is shown in FIG. 2 apparatus for measuring the rate of release of BSA from the polymeric bodies described above. A 1 $cm^2$ square slab, or a hemisphere, is placed in a glass scintillation vial containing a 10 ml saline solution. Half of the vials (A in FIG. 2) are designated for exposure to the field of an oscillating bar magnet, and the other half are controls (B in FIG. 2).

A test and control vial are placed on a fixed shelf 20 situated above a magnet triggering device 22. The device is a commercial speed-controlled rocker (Minark Electric Co., Los Angeles, Calif.) having a motor 30 arranged to rock table 28. A bar magnet 24 and counter weight 26 are placed at opposite ends of table 28.

The vials are allowed to sit for 72 hours with the rocker off to allow any initial release burst. The rocker is then turned on for a six-hour period at a frequency of 18 cycles per minute, subjecting the test vial to an oscillating magnetic field ranging from 0.5 gauss (the magnetic field strength on the surface of the earth) to approximately 1,000 gauss. The control vial is far enough from the bar magnet that it experiences no significant magnetic field oscillations. The rocker is turned off for six hours and the six hour on-and-off cycle is continued for 130 hours.

Figure 3:
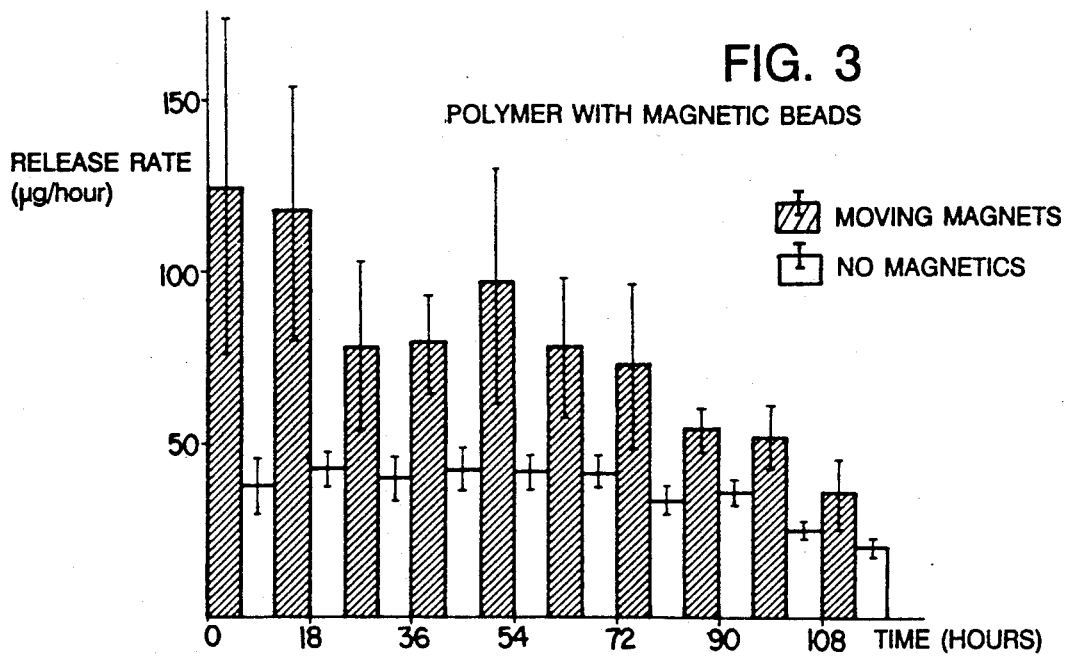
FIG. 3 is a graph illustrating the effect of exposure to an oscillating magnetic field on the rate of release of a biologically active substance from a preferred composition.

The histogram of FIG. 3 shows that, in the case of the slabs prepared according to the method illustrated in FIG. 1, the rate of release is significantly increased by magnetically stimulating the bodies, for a period of time up to 108 hours. For example, the first six-hour exposure period showed an average release rate of about 125 $\mu$g/hour compared to about 40 $\mu$g/hour in the following six hours of no exposure. The differential decreased with increasing time but was still significant at 108 hours.

The histogram of FIG. 7 shows that magnetic stimulation also increases release rate from the hemispheric bodies. Release rate is measured in the presence and absence of hourly magnetic stimulation over a 10 day period. The average release rate, absent stimulation, is 14.8 $\mu$g/hour, compared to an average rate of 424.1 $\mu$g/hour upon exposure to magnetic stimulation. This increase, 29 fold, is greater than that observed for the square slabs containing dispersed beads. The hemispheric shape also provides a rate of release which is independent of drug concentration, even at low concentrations.

OTHER EMBODIMENTS

Other embodiments are within the following claims. For example, any biologically active substance can be used, in conjunction with any biologically compatible, water-insoluble polymer and any organic solvent capable of dissolving the polymer. The active substance can be protein or it can be non-proteinaceous, and it can be a macromolecule (M.W. over 1000 daltons) or a smaller molecule. Examples of suitable active substances are interferon, anti-angiogenesis factors, antibodies, antigens, polysaccharides, growth factors, hormones, including insulin, glucagan, parathyroid, and pituatary hormones, calcitonin, vasopressin, renin, prolactin, growth hormones, thyroid stimulating hormone, corticotrophin, follicle stimulating hormone, luteinising hormone, and chorionic gonadatrophin; enzymes, including soybean trypsin inhibitor, lysozyme, catalase, tumor angiogenesis factor, cartilege factor, transfereses, hydrolases, lysases, isomerases, proteases, ligases, and oxidoreductases such as esterases, phosphatases, glycosidases, and peptidases; enzyme inhibitors such as leupeptin, antipain, chymostatin, and pepstatin; and drugs.

Suitable polymers include acyl substituted cellulose acetates and alkyl derivatives thereof; partially and completely hydrolyzed alkylene-vinyl acetate copolymers; unplasticized polyvinyl chloride; crosslinked homo- and co-polymers of polyvinyl acetate; crosslinked polyesters of acrylic and methacrylate; polyvinyl alkyl ethers; polyvinyl fluoride; silicone; polycarbonate; polyurethane; polyamide; polysulphones; styrene acrylonitrile copolymers; crosslinked poly(ethylene oxide); poly(alkylenes); poly(vinyl imidazole); poly(esters); poly(ethylene terephthalate); and chlorosulphonated polyolefins.

EVA, the most preferred polymer, is a member of a class of suitable polymers of the general formula $$\left(\begin{array}{c}\phantom{x}\\O\\|\\C=O\\|\\R\end{array}\right)_m \left(\phantom{xx}\right)_n$$

wherein R is hydrogen, lower alkyl of 1 to 7 carbons or aryl, and m is (10 to 40) % by weight and n is (100-m) % by weight. Typical alkyl groups include ethyl, propyl, isopropyl, tert-butyl, pentyl, and hexyl. Suitable ethylene-vinyl ester copolymers are the acetates, include ethylene-vinyl acetate, ethylene-vinyl methylacetate, ethylene-vinyl ethylacetate, ethylene-vinyl propylacetate, and the like.

Polymer bodies can be made, according to the method of the invention, in any desired shape; the shape will sometimes be determined by the body's location.

Polymer bodies made according to the method of the invention are implanted in animals, including humans, to provide controlled, prolonged release of the desired biologically active substance. Some medical applications of these polymer bodies are the prolonged release of insulin for the control of diabetes, immunizations (the active substance is an antigen), the delivery of informational macromolecules for assays for biological molecules such as tumor angiogenisis factor, and the prolonged treatment of a variety of medical disorders with the appropriate drugs.

We claim:

1. A method of administering a biologically active substance to an animal, e.g., a human, said method comprising
preparing an implant for said animal of a medically responsive composition in the form of a body sized and shaped for placement in the environment of use, said environment including an aqueous fluid, said body comprising, in admixture, a first phase comprising a biocompatible, plastically deformable, polymeric matrix, said polymeric matrix being insoluble in the environment of use, a second phase comprising a biologically active substance distributed throughout said matrix to be released to said aqueous fluid outside said matrix, and a third phase comprising a magnetically responsive substance encapsulated within said matrix so that, upon exposure of said body to an oscillating magnetic field, the rate of release of said biologically active substance to said aqueous fluid is increased,
in order to subject said body in said animal to an oscillating magnetic field which creates sufficient disturbance to increase the rate of release of said biologically active substance.

2. The method of claim 1 wherein said magnetically responsive substance is in the form of discrete particles dispersed throughout said matrix.

3. The method of claim 1 wherein said magnetically responsive substance is in the form of a single piece.

4. The method of claim 1 wherein said magnetically responsive substance is a metal.

5. The method of claim 4 wherein said magnetically responsive substance is stainless steel.

6. The method of claim 3 wherein said magnetically responsive substance is a permanent magnet.

7. The method of claim 2 wherein said particles are beads between 0.8 and 1.4 mm in diameter.

8. The method of claim 1 wherein the ratio, by weight, of said biologically active substance to said polymer is between 1:99 and 90:10.

9. The method of claim 1 wherein said active substance has a molecular weight of at least 150 daltons.

10. The method of claim 9 wherein said active substance is a protein.

11. The method of claim 1 wherein said active substance is a peptide hormone selected from the group consisting of insulin, glucagon, parathyroid, pituitary, calcitonin, vasopressin, renin, prolactin, growth, thyroid stimulating, corticotrophin, follical stimulating, luteinising and chorionic gonadotrophin hormones.

12. The method of claim 11 wherein said peptide hormone is insulin.

13. The method of claim 1 wherein said active substance is a steroid.

14. The method of claim 1 wherein said polymeric matrix is an ethylene vinyl ester copolymer of the general formula:

$$\left(\begin{array}{c}\phantom{x}\\O\\|\\C=O\\|\\R\end{array}\right)_m \left(\phantom{xx}\right)_n$$

wherein R is a member selected from the group consisting of hydrogen, lower alkyl of 1 to 7 carbons, and aryl; m is 10 to 40% by weight, and n is (100-m) % by weight.

15. The method of claim 1, wherein said polymeric matrix is a crosslinked polymeric matrix.

* * * * *

UNITED STATES PATENT AND TRADEMARK OFFICE
CERTIFICATE OF CORRECTION

PATENT NO. : 5,019,372
DATED : MAY 28, 1991
INVENTOR(S) : JUDAH FOLKMAN, ROBERT S. LANGER, JR., DEAN S. T. HSIEH

It is certified that error appears in the above-identified patent and that said Letters Patent is hereby corrected as shown below:

column 1, line 22, before "BACKGROUND OF THE INVENTION" insert --This invention was made with government support under Grant No. RO1 GM 26698-01 by the NIH. The government has certain rights in the invention.--

Signed and Sealed this

Tenth Day of April, 2001

*Attest:*

NICHOLAS P. GODICI

*Attesting Officer*  *Acting Director of the United States Patent and Trademark Office*